United States Patent
Zhang et al.

(10) Patent No.: US 8,141,441 B2
(45) Date of Patent: Mar. 27, 2012

(54) HAND-HELD SAMPLING DEVICE PREVENTING DEFORMATION OF SAMPLING WIPE AND METHOD OF USE THEREOF

(75) Inventors: Yangtian Zhang, Beijing (CN); Jianhua Liu, Beijing (CN); Yaoxin Wang, Beijing (CN); Hua Peng, Beijing (CN)

(73) Assignee: Nuctech Company Limited, Beijing (CN)

( * ) Notice: Subject to any disclaimer, the term of this patent is extended or adjusted under 35 U.S.C. 154(b) by 418 days.

(21) Appl. No.: 12/228,054

(22) Filed: Aug. 7, 2008

(65) Prior Publication Data

US 2009/0078063 A1 Mar. 26, 2009

(30) Foreign Application Priority Data

Aug. 10, 2007 (CN) .................... 2007 1 0120177

(51) Int. Cl.
*G01N 1/04* (2006.01)
(52) U.S. Cl. ................................. 73/864.71
(58) Field of Classification Search ............... 73/863.31, 73/864.71
See application file for complete search history.

(56) References Cited

U.S. PATENT DOCUMENTS

| | | | |
|---|---|---|---|
| 5,859,375 A * | 1/1999 | Danylewych-May et al. | 73/864.71 |
| 5,988,002 A | 11/1999 | Danylewych-May et al. | |
| 6,321,408 B1 * | 11/2001 | Esterson et al. | 15/176.2 |
| 2007/0137319 A1 * | 6/2007 | Nacson et al. | 73/864 |

FOREIGN PATENT DOCUMENTS

| | | |
|---|---|---|
| FR | 2 708 740 | 2/1995 |
| GB | 2 280 133 | 1/1995 |
| SU | 927029 | 8/1991 |
| WO | WO 2007/069088 | 6/2007 |

OTHER PUBLICATIONS

United Kingdom Search Report of Application No. GB0814575.7, dated Nov. 19, 2008.

(Continued)

*Primary Examiner* — Hezron E Williams
*Assistant Examiner* — Nathaniel Kolb
(74) *Attorney, Agent, or Firm* — Kenyon & Kenyon LLP

(57) ABSTRACT

A hand-held sampling apparatus used for an ion mobility spectrometer and method of obtaining a sample are provided to prevent deformation of sampling wipes when detecting explosives and drugs. The apparatus has a body comprising a handle in the rear portion and a wiping sampling mechanism in the front portion, with a wiping surface located on its underside. The sampling wipe can be in full contact with the surface of the object during wiping to improve wiping efficiency. Correspondingly, a smaller sample inlet port can be disposed on the analyzer so as to save a large amount of sampling wipes. and meanwhile avoid sampling wipes from deformation and folds hard to restore, thereby ensuring subsequent sample insertion operation, enhancing the efficiency of both sample collection and sample injection and improving the detection performance for the analytes to be detected. The method of using said sampling device according to the present invention comprises the following steps: attaching a sampling wipe to the swiping surface; fixing the front end portion of the sampling wipe by using the front holder, and fixing the rear end portion of the sampling wipe by using the rear holder. The method of the present invention is simple and convenient.

11 Claims, 1 Drawing Sheet

OTHER PUBLICATIONS

Russian Office Action issued in Russian Application No. 2008132849, with English translation.
German Examination Report dated Jan. 10, 2011 issued in corresponding German Application No. 10 2008 038 869.6.
UK Search and Examination Report dated Nov. 20, 2008 issued in corresponding UK Application No. GB0814575.7.
Japanese Examination Report dated Mar. 1, 2011 issued in corresponding Japanese Application No. 2008-198010.
Chinese Office Action dated Jan. 29, 2010 issued in corresponding Chinese Application No. 2007101201775.
Chinese Office Action dated May 28, 2010 issued in corresponding Chinese Application No. 2007101201775.

* cited by examiner

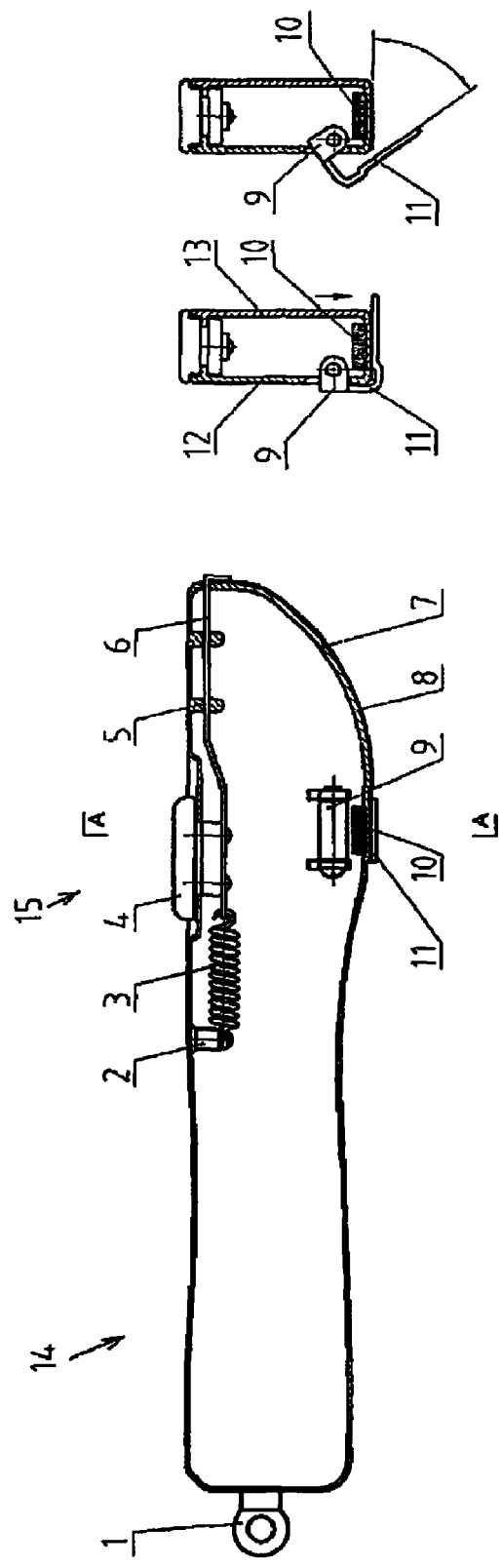

HAND-HELD SAMPLING DEVICE PREVENTING DEFORMATION OF SAMPLING WIPE AND METHOD OF USE THEREOF

RELATED APPLICATION

This application claims priority to Chinese Patent Application No. 200710120177.5, filed Aug. 10, 2007, which is incorporated herein by reference in its entirety.

FIELD OF THE INVENTION

This invention relates to a sampling device and a method of using the same, particularly to a hand-held wiping sampling device for collection of samples from surfaces of an object when an ion mobility spectrometer detects explosives and drugs.

BACKGROUND OF THE INVENTION

An explosives and drugs detector based on ion mobility spectrometry is a quick, sensitive and portable on-site detection instrument which has been applied for military purposes or used by security inspection organizations to detect chemical warfare agents, explosives, drugs, etc.

When an ion mobility spectrometer detects contraband compounds, in addition to a vapor sampling mode (generally called "odor smelling" mode), particle sampling is the most commonly used sampling mode. By adopting the particle sample collection mode, a sampling wipe is first used to wipe the surface of an object to collect particulates of explosives or drugs, and then the wipe is inserted into the sample inlet port of the instrument for detection and identification.

Currently particle sampling for an ion mobility spectrometer is conducted in two modes:

1. Direct Wiping

In this mode, an operator manually holds the sampling wipe to directly wipe the surface of an object. To avoid the hand from contacting the surface of the object (the contaminated hand may interfere with the subsequent sampling and detection), the sampling wipe has to be made very large and correspondingly the sample inlet port of the instrument is also made very large. This will not only cause great waste of sampling wipes, and, more importantly, such a very large sample inlet port has a lot of drawbacks: firstly, uncentralized heat and the resultant low heating efficiency adversely affect the sensitivity of the instrument; secondly, a large electrical power consumption shortens the working time of the battery so that the battery needs to be replaced frequently, thus affecting the application performance of the instrument.

2. Wiping Using a Sampling Device

At present, there is a kind of apparatus which can hold a sampling wipe for sample swiping. A paper holder like a paper clip is provided at the front end of the apparatus and opens forwardly. After the front end of the sampling wipe is fixed, it must be folded backwardly 180 degrees to be fixed on the wiping means. Therefore the front end of the sampling wipe forms an obvious fold. The sampling wipe must be restored to a flat and straight state after the sampling wipe is folded so that the sampling wipe can be easily inserted into the sample inlet port. Common plant fiber paper can hardly be restored to the flat and straight state after being folded. For this reason, the wiping means uses specially prepared sampling "paper" (chemical polymer) which is costly to use and exhibits a low sampling efficiency which may affect the detection performance of the instrument. In addition, the wiping contact surface of the wiping means is a flat surface so that when being used to wipe the surface of the object with a certain curvature, the sampling wipe cannot sufficiently contact the surface of the object, thus affecting the wiping and sampling efficiency.

SUMMARY OF THE INVENTION (1) Technical Problems to be Solved

An objective of the present invention is to provide a hand-held wiping sampling device which can save paper, improve the sampling efficiency and meanwhile optimize and improve the sample injection efficiency of an ion mobility spectrometer, to overcome the above drawbacks in the prior art.

(2) Technical Solutions

To achieve the above objective, the present invention uses the following technical solutions:

The hand-held wiping sampling device according to the present invention has a body comprising a handle in the rear portion and a wiping sampling mechanism in the front portion with a wiping surface located on its underside, wherein said wiping surface is a curved surface, e.g., a smoothly transitioning continuous curved surface which resembles the curved surface of a person's fingertip. A sampling wipe can be mounted on the continuous curved surface.

The sample wiping surface can be provided with a front holder at the front side thereof and with a rear holder at the rear side thereof. The two holders are used to hold and secure the sampling wipe.

The wiping sampling portion can be provided with a guide slideway. The front holder can comprise an operation button mounted in said guide slideway that is slideable along said guide slideway, an elastic pressing piece connected on the operation button, and a pre-tension spring whose one end is connected to the elastic pressing piece and the other end is secured to the wiping sampling portion via a spring fastener. The front end portion of the elastic pressing piece can extend out of the wiping sampling portion, and the extended portion is shaped to closely match the contour of the outer surface of the wiping sampling portion. A guide block can be provided in the upper portion of the wiping sampling portion to guide the elastic pressing piece. The front holder is pushed apart from and closed on the sample wiping surface via the elastic pressing piece and forward and backward sliding of the operation button rigidly connected thereto.

The rear holder can comprise a rotatable base rotatably mounted to a side surface of the wiping sampling portion, a rotatable pressing sheet fixed to the rotatable base, and a magnet embedded in the interior of the wiping sampling portion and cooperating with the rotatable pressing sheet. The rear holder can be engaged to and disengaged from the sampling wiping surface via the rotation of the rotatable pressing sheet.

Said rotatable pressing sheet can be L shaped.

In one embodiment, said body comprises a left body and a right body which are snap-fitted together.

A hanging ring can be provided at the rear end portion of the handgrip portion.

In one embodiment, the method of using the handheld wiping sampling device according to the present invention comprises the following steps:

A) applying a sampling wipe to a sampling wiping surface;

B) pushing the operation button of the front holder forward to make the portion of the elastic pressing piece extending out of the body apart from the sampling wiping surface by a certain gap; sandwiching the front end edge of the sampling wipe between the elastic pressing piece and the sampling wiping surface, releasing the operation button so that the front end edge of the sampling wipe is firmly held;

C) turning the rotatable pressing sheet of the rear holder so that the rear end edge of the sampling wipe is firmly held between the rotatable pressing sheet and the sampling wiping surface.

(3) Advantageous Effects

The merits and advantageous effects of the handheld wiping sampling device according to the present invention are: since the sampling wiping surface is a smoothly transitioning continuous curved surface, the sampling wipe can be in full contact with the surface of the object during wiping and improve wiping efficiency, and correspondingly a smaller sample feeding port can be disposed on the detection instrument so as to save a lot of sampling wipes, avoid the sampling wipe from deformation and winkles which are hard to be restored to a flat and smooth state, ensure subsequent sample feeding operation, enhance sampling efficiency and sample feeding efficiency and improve the detection performance of the sample detected.

BRIEF DESCRIPTION OF THE ACCOMPANYING DRAWINGS

FIG. 1 is a schematic view showing the structure of the hand-held wiping sampling device according to the present invention.

FIG. 2 is a cross sectional view taken along the line A-A of FIG. 1, wherein a rotatable pressing sheet is in a closed state.

FIG. 3 is a cross sectional view taken along the line A-A of FIG. 1, wherein the rotatable pressing sheet is in an opened state.

In the figures, 1 hanging ring; 2 spring fastener; 3 pre-tension spring; 4 operation button; 5 guide block; 6 elastic pressing piece; 7 sampling wiping surface; 8 sampling wipe; 9 rotatable base; 10 magnet; 11 rotatable pressing sheet; 12 left body; 13 right body; 14 handgrip portion; 15 wiping sampling portion.

DETAILED DESCRIPTION OF PREFERRED EMBODIMENTS

The following embodiments are used to illustrate the present invention but not used to limit the scope of the present invention.

As shown in FIGS. 1, 2 and 3, the hand-held wiping sampling device according to the present invention comprises a body comprised of a left body 12 and a right body 13 connected together, for example in a snap-fitting mode or in other connection modes. Certainly a person skilled in the art can conceive an integrally formed body. A rear portion of the body is a handgrip portion 14, a front portion of the body is a wiping sampling portion 15, the underside of the wiping sampling portion 15 is a sampling wiping surface 7 which is provided with a front holder at the front side and with a rear holder at the rear side. Said sampling wiping surface 7 is a smoothly transitioning continuous curved surface such as a circular arc surface, the continuous curved surface resembling a curved surface of a person's fingertip. In practical use, the sampling wiping surface 7 abuts closely against a sampling wipe 8. The front and rear holders are used to hold and secure the sampling wipe 8 of the object to be wiped. In the present invention, the wiping sampling portion 15 is provided with a guide slideway. The front holder is comprised of an elastic pressing piece 6, an operation button 4, an pre-tension spring 3 and a spring fastener 2, wherein the operation button 4 is mounted in said guide slideway and slides along said guide slideway, the elastic pressing piece 6 is connected to the operation button 4, the front end portion of the elastic pressing piece 6 extends out of the wiping sampling portion 15, and the extended portion is shaped to contour to an outer surface of the wiping sampling portion 15. One end of the pre-tension spring 3 is connected to the elastic pressing piece 6 and the other end thereof is fixed to the wiping sampling portion 15 via the spring fastener 2. A guide block 5 can be provided in the upper portion in the wiping sampling portion 15 to guide the elastic pressing piece 6. The number of guide block 5 is not limited to one or two and can be determined according to the length of the wiping sampling portion 15. The elastic pressing piece 6 is tightly pulled by the pre-tension spring 3 to achieve securement of the sampling wipe 8 to the front end of the sampling wiping surface 7. A person skilled in the art can conceive a front holder in other form.

The rear holder according to the present invention comprises a rotatable base 9 rotatably connected to a side surface of the wiping sampling portion 15 and a rotatable pressing sheet 11 fixed to the rotatable base 9. A magnet 10 is embedded in the body at a position corresponding to the rotatable pressing sheet 11. The rotatable pressing sheet 11 is made of a material such as iron that can be attracted by the magnet. The other end of the sampling wipe 8 is secured to said sampling wiping surface 7 in a manner that the magnet 10 attracts the rotatable pressing sheet 11 to close. A person skilled in the art can conceive a rear holder in other form, for example, the rear holder is realized via the torsion spring.

In a preferred embodiment, the body of the present invention comprises a left body 12 and a right body 13 detachably mounted together. A hanging ring 1 is provided at the rear end of the body to facilitate pickup and storage of the sampling device in an unoperating state.

The method of using the hand-held wiping sampling device according to the present invention is described as follows. When the device is used, the rotatable pressing sheet 11 (see FIGS. 2 and 3) of the rear holder is rotated first to overcome the attraction force of the magnet 10 and break away from the outer surface of the sampling wiping surface 7; the operation button 4 is pushed forward to make the portion of the elastic pressing piece 6 extending out of the body away from the sampling wiping surface 7 by a certain gap. The front end edge of the sampling wipe 8 is sandwiched between the elastic pressing piece 6 and the sampling wiping surface 7. The operation button 4 is released so that the front end edge of the sampling wipe 8 is firmly held under the action of the pre-tension spring 3. The sampling wipe 8 is made to abut against the sampling wiping surface 7. Then the rotatable pressing sheet 11 is turned reversely to press the sampling wiping surface 7. Due to the attraction of the magnet 10, the rear end edge of the sampling wipe 8 is firmly held. Upon completion of sampling, the rotatable pressing sheet 11 is turned and the operation button 4 is pushed forward so that the sampling wipe 8 is removed from the sampling wiping surface 7 for detection.

The method of using the hand-held wiping sampling device according to the present invention may comprise the steps of: first attaching the sampling wipe 8 to the sampling wiping surface 7, then fixing the front end portion of the sampling wipe 8, and finally fixing the rear end portion of the sampling wipe 8, alternatively, first fixing the rear end portion of the sampling wipe 8, and then fixing the front end portion of the sampling wipe 8.

What is claimed is:

1. A hand-held wiping sampling device, comprising
a body, wherein a rear portion of said body is a handgrip portion (14), and a front portion of the body is a wiping sampling portion (15), the wiping sampling portion (15) comprising on its underside a sampling wiping surface (7), wherein said sampling wiping surface (7) is a smoothly transitioning continuous curved surface; and
a front holder adapted to hold and secure a sampling wipe (8) at the tip end of said sampling wiping surface and a rear holder adapted to hold and secure said sampling wipe at the end of said sampling wiping surface opposite to said tip end.

2. The hand-held wiping sampling device as claimed in claim 1, wherein the wiping sampling portion (15) further comprises a guide slideway, wherein the front holder further comprises an operation button (4) mounted in said guide slideway and slideable along said guide slideway, wherein an elastic pressing piece (6) is connected to the operation button (4), and a pre-tension spring (3) whose one end is connected to the elastic pressing piece (6) and the other end is secured to the wiping sampling portion (15) via a spring fastener (2), wherein the front end portion of the elastic pressing piece (6) can be extended out from the wiping sampling portion (15), and the extended portion is shaped to closely match the contour of the outer surface of the wiping sampling portion (15).

3. The hand-held wiping sampling device as claimed in claim 2, further comprising a guide block (5) in the upper portion of the wiping sampling portion (15) to guide the elastic pressing piece (6).

4. The hand-held wiping sampling device as claimed in claim 2, further comprising in the rear holder a rotatable base (9) rotatably mounted to a side surface of the wiping sampling portion (15), a rotatable pressing sheet (11) fixed to the rotatable base (9), and a magnet (10) embedded in the interior of the wiping sampling portion (15) and cooperating with the rotatable pressing sheet (11).

5. The hand-held wiping sampling device as claimed in claim 4, wherein said rotatable pressing sheet (11) is L shaped.

6. A method of using the handheld wiping sampling device as claimed in claim 4 or 5, comprising the following steps of:
a) providing a sampling wipe (8) to the sampling wiping surface (7);
b) pushing the operation button (4) of the front holder forward to make the portion of the elastic pressing piece (6) extending away from the sampling wiping surface (7);
c) inserting the front end edge of the sampling wipe (8) between the elastic pressing piece (6) and the sampling wiping surface (7);
d) releasing the operation button (4) so that the front end edge of the sampling wipe (8) is firmly held; and
e) turning the rotatable pressing sheet (11) of the rear holder so that the rear end edge of the sampling wipe (8) is firmly held between the rotatable pressing sheet (11) and the sampling wiping surface (7).

7. The hand-held wiping sampling device as claimed in claim 1, further comprising in the rear holder a rotatable base (9) rotatably mounted to a side surface of the wiping sampling portion (15), a rotatable pressing sheet (11) fixed to the rotatable base (9), and a magnet (10) embedded in the interior of the wiping sampling portion (15) and cooperating with the rotatable pressing sheet (11).

8. The hand-held wiping sampling device as claimed in claim 7, wherein said rotatable pressing sheet (11) is L shaped.

9. The hand-held wiping sampling device as claimed in claim 1, wherein said body comprises a left body (12) and a right body (13) which are snap-fitted together.

10. The hand-held wiping sampling device as claimed in any one of claims 1 and 2, further comprising a hanging ring (1) at the rear end portion of the handgrip portion (14).

11. The hand-held wiping sampling device as claimed in claim 1, wherein the wiping sampling portion comprises a planar topside.

* * * * *